US010369161B2

(12) United States Patent
DeLuca et al.

(10) Patent No.: US 10,369,161 B2
(45) Date of Patent: Aug. 6, 2019

(54) USE OF 2-METHYLENE-19-NOR-(20S)-1-ALPHA, 25-DIHYDROXYVITAMIN D3 TO TREAT PRIMARY HYPERPARATHYROIDISM

(71) Applicant: Wisconsin Alumni Research Foundation, Madison, WI (US)

(72) Inventors: Hector F. DeLuca, Deerfield, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 364 days.

(21) Appl. No.: 14/710,744

(22) Filed: May 13, 2015

(65) Prior Publication Data

US 2016/0184327 A1    Jun. 30, 2016

Related U.S. Application Data

(60) Provisional application No. 62/098,119, filed on Dec. 30, 2014.

(51) Int. Cl.
*A61K 31/593*    (2006.01)

(52) U.S. Cl.
CPC .................... *A61K 31/593* (2013.01)

(58) Field of Classification Search
None
See application file for complete search history.

(56) References Cited

U.S. PATENT DOCUMENTS

| | | |
|---|---|---|
| 5,843,928 A | 12/1998 | Deluca et al. |
| 6,136,799 A | 10/2000 | Li et al. |
| 7,563,783 B2 | 7/2009 | DeLuca et al. |
| 2002/0028830 A1 | 3/2002 | Deluca et al. |
| 2005/0124591 A1 | 6/2005 | Tian et al. |
| 2005/0187201 A1 | 8/2005 | DeLuca et al. |
| 2006/0003973 A1 | 1/2006 | DeLuca et al. |
| 2006/0135492 A1 | 6/2006 | DeLuca et al. |
| 2006/0171983 A1 | 8/2006 | Tian et al. |
| 2010/0087404 A1 | 4/2010 | Mazess et al. |
| 2011/0034426 A1 | 2/2011 | Deluca et al. |
| 2014/0005152 A1 | 1/2014 | DeLuca et al. |

FOREIGN PATENT DOCUMENTS

| | | |
|---|---|---|
| JP | 2002543115 | 12/2002 |
| JP | 2003528833 | 9/2003 |
| JP | 2007508298 | 4/2007 |
| JP | 2007523162 | 8/2007 |
| WO | 0066098 | 11/2000 |
| WO | 0172292 | 10/2001 |
| WO | 0205823 | 1/2002 |
| WO | 2005039592 | 5/2005 |
| WO | 2005082456 | 9/2005 |
| WO | 2011119610 | 9/2011 |

OTHER PUBLICATIONS

Shevde et al. (PNAS, 2002, 99, 13487-13491).*
Khan et al. (CMAJ, 2000, 16, 184-187).*
Mischis-Troussard et al. (Q J Med., 2000, 93, 365-367).*
Taniegra (Am Fam Physician, 2, 333-339, 2004).*
Shevde et al., "A potent analog of 1alpha,25-dihydroxyvitamin D3 selectively induces bone formation", PNAS, 99:21, 13487-13491, Oct. 15, 2002.
Slatopolsky et al., Am. J. Kidney Dis. vol. 26, No. 5, 1995: pp. 852-860.
Zella et al., Novel, Selective Vitamin D Analog Suppresses Parathyroid Hormone in Uremic Animals and Postmenopausal Women, Am J. Nephrology 2014; 39:476-483, May 17, 2014.
DeLuca, Hector F. "The Development of a bone-and parathyroid-specific analog of vitamin D: 2-methylene-19-Nor-20S)-1[alpha], 25-dihydroxyvitamin D3", Bonekey Reports, vol. 3, Mar. 5, 2014.
International Search report for International Application No. PCT/US2015/065174, dated Mar. 8, 2016.
Marotta et al. "Potential role of cinacalcet hydrochloride in sporadic primary hyperparathyrodism without surgery indication", Endocrine, Humana Press, Inc., US, vol. 49, No. 1, Aug. 15, 2014, pp. 274-278.
Written Opinion of the International Searching Authority for International Application No. PCT/US2015/065174, dated Mar. 8, 2016.
Advisory Action for U.S. Appl. No. 12/845,173 dated Aug. 28, 2014.
Advisory Action for U.S. Appl. No. 12/845,173 dated Oct. 21, 2013.

(Continued)

*Primary Examiner* — Dennis Heyer
*Assistant Examiner* — Daniel M Podgorski
(74) *Attorney, Agent, or Firm* — Quarles & Brady LLP (57) ABSTRACT

Disclosed are methods of administering 2-methylene-19-nor-(20S)-1α,25-dihydroxyvitamin $D_3$ to treat primary hyperparathyroidism and/or to treat and/or prevent the symptoms of primary hyperparathyroidism in as subject having or at risk for developing primary hyperparathyroidism, preferably without inducing hypercalcemia in the patient.

8 Claims, 3 Drawing Sheets

(56) References Cited

OTHER PUBLICATIONS

Barycki et al., "Removal of the 20-methyl group from 2-methylene-19-nor-(20S)-1alpha,25-dihydroxyvitamin D(3) (2MD) selectively eliminates bone calcium mobilization activity," Bioorg Med Chem., Nov. 15, 2009, 17 (22):7658-69.
Bradford, Marion M., "A Rapid and Sensitive Method for the Quantitation of Microgram Quantities of Protein Utilizing the Principle of Protein-Dye Binding", Analytical Biochemistry, 1976, 72: 248-254.
Brown et al., "The Noncalcemic Analogue of Vitamin D, 22-Oxacalcitriol, Suppresses Parathyroid Hormone Synthesis and Secretion", J. Clin. Invest., 1989, 84: 728-732.
Chen et al, "Modulatory Effects of 1,25-Dihydroxyvitamin D3 on Human B Cell Differentiation", The Journal of Immunology, 2007, 179: 1634-1647.
Curriculum Vitae for Hector F. DeLuca.
Darwish et al., "Identification of a Transcription Factor That Binds to the Promoter Region of the Human Parathyroid Hormone Gene", Archives of Biochemistry and Biophysics, 1999, 365(1): 123-130.
Declaration for U.S. Appl. No. 12/845,173 dated Sep. 27, 2013.
DeLuca H.F. "Therapeutic potential of the 2-aklyl and 2-alkylidene-19-nor-(20S)-odified analogs of 1-25-dihydroxyvitamin D3." Journal of Steroid Biochemistry & Molecular Biology 89-90 (2004) 67-73.
DeLuca, "The development of a bone- and parathyroid-specific analog of vitamin D: 2-methylene-19-Nor-(20S)-1alpha,25-dihydroxyvitamin D3," Bonekey Rep, Mar. 5, 2014, 2:514.
DeLuca et al., "The vitamin D analogue 2MD increases bone turnover but not BMD in postmenopausal women with osteopenia: results of a 1-year phase 2 double-blind, placebo-controlled, randomized clinical trial," J Bone Miner Res., Mar. 2011, 26(3):538-545.
DeLuca et al., "Vitamin D: The Vitamin and the Hormone", Fed. Proc., 1974, 33: 2211-2219.
Delmez, et al., "Hyperphosphatemia: Its Consequences and Treatment in Patients with Chronic Renal Disease", American Journal of Kidney Diseases, 1992, XIX(4): 303-317.
Demay et al., "Sequences in the Human Parathyroid Hormone Gene that Bind the 1,25-Dihydroxyvitamin D3 Receptor and Mediate Transcriptional Repression in Response to 1,25-Dihydroxyvitamin D3", Proc. Natl. Acad. Sci. USA, 1992, 89: 8097-8101.
Final Office Action for U.S. Appl. No. 12/845,173 dated Mar. 31, 2014.
Final Office Action for U.S. Appl. No. 12/845,173 dated Jul. 3, 2013.
International Preliminary Report on Patentability for PCT/US2010/043551 dated Feb. 7, 2012.
International Search Report and Written Opinion in PCT/US2010/043551, filed Jul. 28, 2010.
International Search Report and Written Opinion, PCT International Application No. PCT/US2013/031574, dated Feb. 11, 2010.
Ke et al., "A New Vitamin D Analog, 2MD, Restores Trabecular and Cortical Bone Mass and Strength in Ovariectomized Rats With Established Osteopenia", Journal of None and Mineral Research, 2005, 20: 1742-1755.
Khan et al., "NPrimary hyperparathyroidism: pathophysiology and impact on bone," CMAJ 2000;163(2):184-7.
Kim, James, "Effects of 1α,25-dihydroxyvitamin D3 on the MRL/mpJ-fas/lpr Model of Systemic Lupus Erythematosus", Ph.D. Thesis, University of Wisconsin-Madison, 2009.
Komaba et al. "Diseases of the parathyroid gland in chronic kidney disease". Clin Exp Nephrol (2011) 15:797-809.
Lopez-Hilker, et al., "Phosphorus Restriction Reverses Hyperparathyriodism in Uremia Independent of Changes in Calcium and Calcitriol", American Journal of Physiology—Renal Physiology, 1990, 259: 432-437.
Meyrier et al., "The Influence of High Calcium Carbonate Intake on Bone Disease in Patients Undergoing Hemodialysis", Kidney International, 1973, 4: 146-153.
Moriniere, et al., "Subtitution of Aluminium Hydroxide by High Doses of Calcium Carbonate in Patients on Chronic Haemodialysis: Disappearance of Hyperaluminaemia and Equal Control of Hyperparathyriodism", Proc. EDTA, 1982, 19: 784-787.
National Kidney Foundation, Inc. Part 4. Definition and Classification of Stages of Kidney Disease, American Journal of Kidney Diseases, vol. 39, No. 2, Suppl 1. Feb. 2002, pp. S46-S75.
Office Action for U.S. Appl. No. 12/845,173 dated Nov. 6, 2014.
Office Action for JP2012-523654 dated Aug. 29, 2014.
Office Action for U.S. Appl. No. 12/845,173 dated Aug. 24, 2012.
Portale, et al., "Effect of Dietary Phosphorus on Circulating Concentrations of 1,25-Dihydroxyvitamin D and Immunoreactive Parathyroid Hormone in Children with Moderate Renal Insufficiency", J. Clin. Invest., 1984, 73: 1580-1589.
Quarles, et al., "Prospective Trial of Pulse Oral Intravenous Calcitriol Treatment of Hyperparathyriodism in ESRD", Kidney International, 1994, 45: 1710-1721.
Response for U.S. Appl. No. 12/845,173 dated Jan. 23, 2013.
Response for U.S. Appl. No. 12/845,173 dated Oct. 2, 2013.
Response for U.S. Appl. No. 12/845,173 dated Apr. 6, 2015.
Response for U.S. Appl. No. 12/845,173 dated Jul. 25, 2014.
Response for U.S. Appl. No. 12/845,173 dated Nov. 4, 2013.
Sato et al., "New 19-nor-(20S)-1alpha,25-dihydroxyvitaimin D3 analogs strongly stimulate osteoclast formation both in vivo and in vitro," Bone, Feb. 2007, 40(2):293-304.
Search Report for SG11201408731W dated Jun. 23, 2015.
Shevde et al., "A potent analog of 1alpha,25-dihydroxyvitamin D3 selectively induces bone formation", PNAS, 2002, 99 (21): 13487-13491.
Sibilska et al., "1-desoxy analog of 2MD: synthesis and biological activity of (20S)-25-hydroxy-2-methylene-19-norvitamin D3," J Steroid Biochem Mol Bio, Jul. 2010, 121(1-2):51-55.
Slatopolsky et al., "Calcium Carbonate as a PHosphate Binder in Patients with Chronic Renal Failure Undergoing Dialysis", New Engl. J. Med., 1986, 315: 157-161.
Slatopolsky et al., "Marked Suppression of Secondary Hyperparathyroidism by Intravenous Administration of 1,25-Dihydroxycholecalciferol in Uremic Patients", J. Clin. Invest., 1984, 74: 2136-2143.
Slatopolsky et al., "New analog of calcitriol, 19-nor-1,25-(OH)2D2, suppresses parathyroid hormone secretion in uremic rats in the absence of hypercalcemia," American Journal of Kidney Diseases, Nov. 1995, 26(5):852-860.
U.S. Appl. No. 09/616,164, filed Jul. 14, 2000.
Vanhooke et al., "New analogs of 2-methylene-19-nor-(20S)-1,25-dihydroxyvitamin D3 with conformationally restricted side chains: evaluation of biological activity and structural determination of VDR-bound conformations," Arch Biochem Biophys, Apr. 15, 2007, 460(2):161-165.
Written Opinion for SG11201408731W dated Aug. 14, 2015.
Yamamoto et al, "2-Methylene-19-nor-(20S)-1alpha,25-dihydroxyvitamin D3 Potently Stimulates Gene-specific DNA Binding of the Vitamin D Receptor in Osteoblasts", Journal of Biological Chemistry, 2003, 278(34): 31756-31765.
Zella et al., "2MD, a Potent and Selective 1,25-Dihydroxyvitamin D Analog, Suppresses PTH in 5/6-Nephrectomized Rats and in Post-menopausal Women", American Journal of Nephrology, Mar. 6, 2014, pp. 1-50.
DeLuca, "Therapeutic potential of the 2-alkyl and 2-alkylidene-19-nor-(20S)-modified analogs of 1alpha,25-dihydroxyvitamin D3" Journal of Steroid Biochemistry & Molecular Biology, 2004, 89-90, 67-73.

* cited by examiner

USE OF 2-METHYLENE-19-NOR-(20S)-1-ALPHA,25-DIHYDROXYVITAMIN D3 TO TREAT PRIMARY HYPERPARATHYROIDISM

CROSS-REFERENCE TO RELATED PATENT APPLICATIONS

The present application claims the benefit under 35 U.S.C. § 119(e) to U.S. Provisional Patent Application No. 62/098,119, filed on Dec. 30, 2014, the content of which is incorporated herein by reference in its entirety.

BACKGROUND

This invention relates to vitamin D compounds useful in treating and/or preventing primary hyperparathyroidism and/or the symptoms thereof, and more particularly to the use of the vitamin D compound 2-methylene-19-nor-(20S)-1α,25-dihydroxyvitamin $D_3$, otherwise referred to herein as "2MD," to treat primary hyperparathyroidism and/or to treat and/or prevent the symptoms thereof.

"Hyperparathyroidism" refers to a disorder of the parathyroid glands in which the parathyroid glands exhibit overactivity. "Primary" hyperparathyroidism means the disorder originates in the parathyroid glands themselves in contrast to "secondary" hyperparathyroidism which means the disorder results subsequent to another underlying disease or disorder such as renal failure.

In primary hyperparathyroidism, the parathyroid glands become overactive and release excessive parathyroid hormone (PTH) into the blood stream. One of the primary functions of PTH is to increase serum calcium levels. When the parathyroid glands sense a low level of calcium in blood serum via calcium receptors (CaRs) present in the parathyroid glands, the parathyroid glands are stimulated to secrete PTH into the blood stream. The PTH secreted into the blood stream causes mobilization of calcium from bones and increased absorption of calcium by the small intestine, both of which result in increasing serum calcium levels. As such, serum PTH levels and serum calcium levels are controlled by a negative feedback mechanism.

Because PTH results in increasing, serum calcium levels, excessive serum PTH results in excessive serum calcium levels or "hypercalceinia," which presents a number of health risks. Hypercalcemia may cause the kidneys to excrete more calcium in the urine, which can lead to kidney stones. Hypercalcemia also might contribute to other problems, such as heart disease, high blood pressure, and difficulty with concentration. Indirect symptoms of mildly elevated serum calcium levels may include joint aches, fatigue, weakness, loss of appetite, mild depression, and difficulty concentrating. In addition to causing hypercalcemia, excessive PTH also may result in weakened hones due to excessive mobilization of calcium from bones.

About 100,000 people in the United State develop primary hyperparathyroidism each year. The disorder is diagnosed most often in people between age 50 and 60, and women are affected more often than men. In particular, primary hyperparathyroidism may be observed in women that have been diagnosed with a bone metabolic disorder such as osteopenia or osteoporosis. In the majority of patient with primary hyperparathyroidism, a benign tumor called an adenoma has formed in the parathyroid glands which causes the glands to become overactive. Less frequently, primary hyperparathyroidism is caused by a malignant tumor or cancer of the parathyroid gland. Parathyroid glands also may become overactive because of lithium therapy, past radiation to the neck, or certain gene defects.

The majority of people with hyperparathyroidism have few or no symptoms. In these people, hyperparathyroidism is typically detected when a blood test is done for some other reason and abnormally high serum calcium levels are observed, which may be due to excessive serum PTH levels. Most often, the serum calcium levels are only mildly elevated or are elevated intermittently. Symptoms become more noticeable as the parathyroid hormone (PTH) and serum calcium levels rise to more severe levels. At higher levels of PTH and serum calcium, there may be a significant loss of appetite, nausea, constipation, excessive thirst, or frequent urination. In addition severely high calcium levels may result in impaired kidney function, kidney stones, bone disease, and rheumatologic symptoms.

In patients exhibiting severely high serum calcium levels due to primary hyperparathyroidism, the most common form of treatment is surgery to remove the overactive parathyroid glands. Non-surgical treatment methods may include modulating calcium intake and supplementing vitamin D intake. Vitamin D deficiency can stimulate PTH secretion and bone resorption, so adequate vitamin D levels are beneficial. In order to treat bone loss, for example osteopenia or osteoporosis, bisphosphonates may be administered.

In order to reduce PTH secretion directly, a calcimimetic also may be administered to treat primary hyperparathyroidism. A calcimimetic is an agent that mimics the effect of calcium on the calcium receptors (CaRs) in the parathyroid gland. As such, calcimimetics increase the sensitivity of the calcium-sensing receptor (CaR) to circulating serum calcium reducing the secretion of PTH and the serum calcium concentration. Calcimimetics include the compound named (R)—N-[1-(1-naphthyl)ethyl]-3-[3-(trifluoromethyl)phenyl]propan-1-amine otherwise referred to as "cinacalcet."

Vitamin D analogs have been approved by the US Food and Drug Administration (FDA) for treating secondary hyper parathyroidism, such as secondary hyperparathyroidism subsequent to renal failure. The kidneys are important for regulating PTH secretion and serum calcium levels because vitamin D is metabolized in the kidneys into its active form which is called "calcitriol." One of the functions of calcitriol is to mobilize calcium from bone and to increase absorption of calcium by the small intestine in order to increase serum calcium levels. Calcitriol and other active vitamin D analogs also decrease the expression and secretion of PTH from the parathyroid glands. (See Slatopolsky et al., Am. J. Kidney Dis. Vol. 26, No. 5, 1995: pp 852-860.) In a patient with renal failure, the kidneys no longer metabolize vitamin D to produce calcitriol, and as a result, the patient no longer has the ability to increase serum calcium levels via the effect of calcitriol. Likewise, the patient no longer has the ability to regulate the expression and secretion of PTH from the parathyroid glands via the effect of calcitriol. When calcitriol and serum calcium levels are low in patients with renal failure, the parathyroid gland secretes excess PTH in order to increase serum calcium levels via mobilizing calcium from bone and increasing absorption of calcium by the small intestine. Because vitamin D analogs have been shown to act on the parathyroid glands and decrease secretion of PTH, vitamin D analogs have been approved by the FDA for treating secondary hyperparathyroidism, including, paraealcitol, which is sold under the trademark Zemplar®. (See also U.S. Published Application No. 2114/0005152, the content of which is incorporated herein by reference in its entirety).

However, no vitamin D analogs have been approved for treating primary hyperparathyroidism. Thus, new vitamin D analogs that can be used to treat primary hyperparathyroidism are highly desirable, including vitamin D analogs that can be administered to reduce PTH secretion. Here, a highly potent active vitamin D analog (AVD), namely, 2-methylene-19-nor-(20S)-1α,25-dihydroxyvitamin $D_3$, otherwise referred to as "2MD" is shown to suppress PTH production in patients having primary hyperparathyroidism without increasing serum calcium or serum phosphate. As such, 2MD is useful for treating primary hyperparathyroidism in patients without increasing serum calcium or serum phosphate.

SUMMARY

It has now been discovered that the vitamin D analog 2-methylene-19-nor-(20S)-1α,25-dihydroxyvitamin $D_3$ (2MD) has the ability to treat primary hyperparathyroidism and symptoms thereof when administered under well-controlled conditions to a subject in need thereof. It also now been discovered that the vitamin D analog 2MD has the ability to treat primary hyperparathyroidism and/or to treat and/or prevent the symptoms thereof when administered under well-controlled conditions to a subject in need thereof.

In one embodiment, the present invention provides a novel method of treating primary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject exhibiting symptoms of primary hyperparathyroidism or at risk for developing primary hyperparathyroidism, preferably without inducing hypercalcemia in the subject.

In another embodiment, the present invention provides a novel method of treating symptoms of primary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject exhibiting symptoms of primary hyperparathyroidism, preferably without inducing hypercalcemia in the subject.

In still another embodiment, the present invention provides a novel method of preventing symptoms of primary hyperparathyroidism by administering a therapeutically effective amount of a composition comprising 2-methylene-19-nor-(20S)-1α,25-dihydroxyvitamin $D_3$ (2MD) or pharmaceutically acceptable salts thereof as the active agent to a subject having, or at risk of developing primary hyperparathyroidism, preferably without inducing hypercalcemia in the subject.

In the disclosed methods, the 2-methylene-19-nor-(20S)-1α,25-dihydroxyvitamin $D_3$ (2MD) may be formulated in an oral, topical, hansdermal, parenteral, injectable or infusable form of a pharmaceutical composition comprising a suitable dose of 2MD. In some embodiments, pharmaceutical compositions may comprise 2MD (or pharmaceutically acceptable salts thereof) in a minimal dose of at least about 0.01, 0.05, 0,1, 0.5, 1.0, 5,0, 10.0, 50.0, 100.0, 500.0 or 1000.0 μg/gm of the composition. In other embodiments, pharmaceutical compositions may comprise 2MD (or pharmaceutically acceptable salts thereof) in a maximal dose no greater than 1000.0, 500.0, 100.0, 50.0, 10.0, 5.0, 1.0, 0.1, or 0.05 μg/gm of the composition. The compositions may comprise 2MD within dose ranges having as end-points any of these disclosed doses (e.g., where 2MD represents 0.01-1000.0 μg/gm of the composition). Minimal and/or maximal doses may be administered at any suitable frequency, such as daily, three times per week, weekly, or other frequencies.

In the disclosed methods, 2-methylene-19-nor-(20S)-1α,25-dihydroxyvitamin (2MD) may be administered at a minimal dose level for achieving therapy. In some embodiments, a minimal dose level for achieving therapy may be at least about 0.1, 0.25, 0.5, 1.0, 2.5, 5.0, 10.0, 12.5, 15.0, or 20.0 ng/kg body weight of the subject. In the disclosed methods, 2MD may be administered at a maximal dose level for achieving therapy without resulting in an undesirable side effect such as hypercalcemia. In some embodiments, a maximal dose level may not exceed about 20.0, 15.0, 12.5, 10.0, 5.0, 2.5, 1.0, 0.5, 0.25, and 0.1 ng/kg body weight of the subject. Minimal and/or maximal dose levels may include dose level ranges having as end-points any of these disclosed dose levels (e.g., 0.1-20.0 ng/kg body weight of the subject).

Patients suitable for the disclosed treatment and prevention methods may include a patient having or at risk for developing primary hyperparathyroidism or the symptoms thereof including a patient previously administered a calcimimetic. For example, patients suitable for the disclosed treatment and prevention methods may include a patient previously administered cinacalcet.

DETAILED DESCRIPTION

Disclosed are methods of treating primary hyperparathyroidism and/or treating and/or preventing the symptoms of primary hyperparathyroidism in a patient in need thereof. The disclosed methods further may described as follows based on the following definitions.

As used in this specification and the claims, the singular forms "a," "an," and "the" include plural forms unless the content clearly dictates otherwise. For example, "an active vitamin D compound" or "AVD," should be interpreted to mean "one or more AVDs," and "a calcimimetic" or "CM" should be interpreted to mean "one or more CMs."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, the term "patient," which may be used interchangeably with the terms "subject" or "individual," refers to one who receives medical care, attention or treatment and may encompass a human patient. The disclosed methods may be utilized to treat primary hyperthyroidism in a patient in need thereof. A patient in need thereof may include, but is not limited to a patient having or at risk for developing primary hyperthyroidism subsequent to a cell hyperplasia or cancer of the parathyroid glands. A patient in need thereof may include, but is not limited to, a patient having or at risk for developing primary hyperthyroidism subsequent to a lithium treatment or radiation treatment of the parathyroid glands.

A patient having primary hyperparatroidism or at risk for developing primary parathyroidism may include a patient having elevated serum parathyroid hormone (PTH) levels that cannot be attributed to a secondary cause (e,g., renal failure). Normal PTH levels typically are within a range of 10-55 pg/ml. As such, a patient having primary hyperparathyroidism or at risk for developing primary parathyroidism may include a patient having serum PTH levels that are greater than about 55, 60, 65, or 70 pg/ml.

The disclosed methods may be utilized to treat and/or prevent the symptoms of primary hyperthyroidism in a patient in need thereof. Symptoms of primary hyperthyroidism treated and/or prevented by the disclosed methods may include, but are not limited, to elevated serum PTH levels, elevated serum calcium levels, joint aches, fatigue, weakness, loss of appetite, mild depression, difficulty concentrating, loss of appetite, nausea, constipation, excessive thirst, frequent urination, impaired kidney function, kidney stones, bone disease, and rheumatologic symptoms.

Calcitriol has been utilized to treat the symptoms of secondary hyperparathyroidism. However, hypercalcemia is a frequent result that accompanies treatment with calcitriol. Hypercalcemia (i.e., increased levels of calcium in the blood) can result in serious physical problems, including death. Specifically, an increase in calcium of approximately 2 mg/100 ml is considered mild hypercalcemia and is not considered a problem. However, an increase in calcium levels of more than 2 mg/100 ml is considered severe hypercalcemia and can cause calcification of the kidney, heart, and aorta. Clearly, the use calcitriol is not optimal to treat or prevent primary hyperparathyroidism, or the symptoms thereof, because of the resultant hypercalcemia observed when calcitriol is utilized to treat secondary hyperparathyroidism.

2-methylene-19-nor-(20S)-1α,25-dihydroxyvitamin $D_3$ (2MD) is an analog of $1,25(OH)_2D_3$ which has been shown to have increased in vivo potency toward bone but not on intestinal calcium absorption. The overall synthesis of 2MD is illustrated and described more completely in U.S. Pat. No. 5,843,928, issued Dec. 1, 1998, and entitled "2-Alkylidene-19-Nor-Vitamin D Compounds" the specification of which is specifically incorporated herein by reference. The biological activity of 2MD is also reported in U.S. Pat. No. 5,843,928 and in Shevde et al., "A Potent Analog of 1α,25-dihydroxyvitamin $D_3$ Selectively Induces Bone Formation" PNAS, Vol. 99, No. 21 pp 13487-13491. (2002), both of which are specifically incorporated herein by reference.

Surprisingly, in the methods disclosed herein, 2MD can be administered to treat primary hyperparathyroidism and/or to treat and/or prevent the symptoms of primary hyperparathyroidism in a patient in need thereof without causing severe hypercalcemia in the patient in need thereof As used herein, "hypercalcemia" means elevated calcium levels in the blood. In a normal subject, calcium levels are approximately 9-10.5 mg/dL or 2.2-2.6 mmol/L. As such, calcium levels greater than about 10.5 mg/dL or 2.6 mmol/L may be indicative of hypercalcemia. In cases of severe hypercalcemia (i.e., calcium levels above 15-16 mg/dL or 3,75-4 mmol/L) coma and cardiac arrest can develop.

The present invention therefore provides novel methods of treating primary hyperparathyroidism and/or treating and/or preventing the symptoms of primary hyperparathyroidism in a subject at risk of developing primary hyperparathyroidism or in a subject exhibiting symptoms of primary hyperparathyroidism. The methods may include administering to the subject a therapeutically effective amount of 2-methylene-19-nor-(20S)-1α,25-dihydroxyvitamin $D_3$ (2MD) or pharmaceutically acceptable salts thereof preferably without inducing hypercalcemia in the subject, where 2MD has the structure (I):

The disclosed methods may include administering 2MD to a patient that previously was administered a calcimimetic (e.g., in order to treat primary hyperparathyroidism and/or to treat and/or prevent the symptoms of primary hyperparathyroidism). In some embodiments of the disclosed methods, administration of the calcimimetic is discontinued after 2MD is administered to the patient. In other embodiments of the disclosed methods, the patient is administered jointly 2MD and a calcimimetic (e.g., in order to treat primary hyperparathyroidism and/or to treat and/or prevent the symptoms of primary hyperparathyrodisim). For example, 2MD may be administered to the patient before, concurrently, or after the calcimimetic is administered to the patient.

As utilized herein, a calcimimetic is an agent that mimics the effect of calcium on the parathyroid gland. As such, calcimimetics increase the sensitivity of the calcium-sensing, receptor (CaR) to circulating serum calcium, reducing the secretion of PTH and the serum calcium concentration. Calcimimetics may include, but are not limited to, the compound named (R)—N-[1-(1-naphthyl)ethyl]-3-[3-(trifluoromethyl)phenyl]propan-1-amine otherwise referred to as "cinacalcet," sold under the trademark "Sensipar®."

As used herein, "preventing" means forestalling a clinical symptom indicative of primary hyperparathyroidism. Therefore, the term "preventing" includes the prophylactic treatment of subjects to guard them from the occurrence of a disease or symptoms of a disease (e.g., elevated levels of serum PTH). Inhibiting or arresting the development of primary hyperparathyroidism includes, for example, inhibiting or arresting the occurrence of elevated levels of serum PTH.

As used herein, "administering" mean introducing a compound into the body, preferably into the systemic circulation, as described in more detail below. Examples include but are not limited to oral, topical, buccal, sublingual, pulmonary, transdermal, transmucosal, as well as subcutaneous, intraperitoneal, intravenous, and intramuscular injection or in the form of liquid or solid doses via the alimentary canal.

As used herein, "therapeutically effective" means an amount of a compound that, when administered to a subject for treating or preventing a disease or the symptoms thereof, is sufficient to effect such treatment of prevention of the disease or the symptoms thereof. A "therapeutically effective amount" will vary depending on the compound, the disease state being treated, the severity or the disease treated, the age and relative health of the subject, the route and form of administration, the judgment of the attending medical or veterinary practitioner, and other factors.

Pharmaceutical compositions for use in the disclosed treatment and prevention methods comprise an effective dose of 2MD as an active ingredient and a suitable carrier. An effective close of 2MD for use in accordance with the disclosed methods is high enough for achieving a desired therapeutic effect and low enough so as not as to cause an undesired side effect (e.g., hypercalcemia). In some embodiments, pharmaceutical composition may comprise 2MD in a minimal dose of at least about 0.01, 0.05, 0.1, 0.5, 1.0, 5.0, 10.0, 50.0, 100.0, 500.0 or 1000.0 µg/gm of the composition. In other embodiments, pharmaceutical composition may comprise 2MD in a maximal dose no greater than 1000.0, 500.0, 100.0, 50.0, 10.0, 5.0, 1.0, 0.1, 0.05 µg/gm of the composition. The compositions may comprise 2MD within dose ranges having as end-points any of these disclosed doses (e.g., 0.01-10000 µg/gm of the composition). Minimal and/or maximal doses may be administered at any suitable frequency, such as daily, three times per week, weekly, or other frequencies.

In the disclosed treatment and prevention methods, as patient in need thereof may be administered an effective dose level of 2MD. An effective dose level of 2MD for use in accordance with the disclosed methods is high enough for achieving a desired therapeutic effect and low enough so as not as to cause an undesired side effect (e.g., hypercalcemia). In some embodiments, a minimal dose level for achieving therapy may be at least about 0.1. 0.25, 0.5, 1.0, 2.5, 5.0, 10.0, 12.5, 15.0, or 20.0 ng/kg body weight of the subject. In some embodiments, a maximal dose level may not exceed about 20.0, 15.0, 12.5, 10.0, 5.0, 2.5, 1.0, 0.5, 0.25, and 0.1 ng/kg body weight of the subject. Minimal and/or maximal dose levels may include dose level ranges having as end-points any of these discloses dose levels (e.g., 0.1-20.0 ng/kg body weight of the subject).

As used herein, "treat," "treating" or "treatment" means amelioration, alleviation or ablation of primary hyperparathyroidism or a clinical symptom indicative of primary hyperparathyroidism. Amelioration, alleviation or ablation of a clinical symptom includes, for example, arresting, reducing the severity of or slowing the progression of or causing the regression of a symptom of primary hyperparathyroidism, for example, lowering the amount of serum PTH, serum phosphorus, or serum creatinine in response to treatment with 2MD. Specifically, treating may include reducing the amount of serum PTH, serum phosphorus, or serum creatinine pre-treatment versus post-treatment by at least about 20%, 30%, 40%, 50%, 60%, 70%, 80%, 90% or more. Other pathological conditions, chronic complications or phenotypic manifestations of primary hyperparathyroidism are known to those skilled in the art and can similarly be used as a measure of treating primary hyperparathyroidism so long, as there is a reduction in the severity of the condition, complication or manifestation associated with the disease.

Effective compound formulations of 2MD are described in U.S. Pat. No. 5,843,928 and include pharmaceutical applications as a solution in innocuous solvents, or as an emulsion, suspension or dispersion in suitable solvents or carriers, or as pills, tablets, capsules combined with solid carriers. Other formulations may also include other pharmaceutically acceptable and nontoxic excipients such as stabilizers, anti-oxidants, binders, coloring agents or emulsifying or taste-modifying agents and extended release formulations.

In one embodiment, 2MD is the active pharmaceutical ingredient (API) administered in the disclosed methods. The API may be formulated in an oral pharmaceutical dosage form as a solution in innocuous solvents, emulsion, suspension or dispersion in suitable solvents or carriers. The API may also be formulated in various oral dosage forms, such as pills, tablets or capsules using suitable pharmaceutical solid carriers. Such pharmaceutical formulations may also contain other pharmaceutically suitable USP-approved inactive ingredients, excipients, such as stabilizers, anti-oxidants, binders, coloring agents, emulsifiers, and/or taste-modifying agents, which are referred to as USP approved inactive pharmaceutical ingredients.

The API may be administered orally, topically, parenterally or transdermally or by inhalation. The compound may be administered by injection or intravenous infusion using suitable sterile solutions. Topical dosage forms may be creams, ointments, patches, or similar vehicles suitable for transdermal and topical dosage forms. Preferably for the treatment of primary hyperparathyroidism, or for the treatment or prevention of the symptoms of primary hyperparathyroidism, the compound 2MD is administered either orally or parenterally (i.v.). The dose may be properly selected in accordance with the specific route of administration. In some embodiments, the patient may be administered a dose as low as 55 ng, 110 ng, 220 ng, 330 ng, 440 ng, 550 ng, or 660 ng, daily or 3 times per week in order to treat primary hyperparathyroidism and/or to treat or prevent the symptoms thereof in a patient. In some embodiments, the patient may be administered a dose as high as 110 ng, 220 ng, 330 ng, 440 ng, 550 ng, 660 ng, or 770 ng, daily or 3 times per week in order to treat primary hyperparathyroidism and/or to treat or prevent the symptoms thereof in a patient. Minimal and/or maximal doses may include dose ranges having as end-points any of these disclosed doses (e.g., 55 ng-770 ng).

The pharmaceutically suitable oral carrier systems (also referred to as drug delivery systems, which are modern technology, distributed with or as a part of a drug product that allows for the uniform release or targeting or drugs to the body) preferably include FDA-approved and/or USP-approved inactive ingredients. Under 21 CFR 210.3(b)(8), an inactive ingredient is any component of a drug product intended to furnish pharmaceutical activity or other direct effect in the diagnosis, or to affect the structure or any function of the body of humans or other animal. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, "oral dosage" forms may include capsules (i.e., a solid oral dosage form consisting of a shell and a filling), whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with a solid or liquid ingredients that can be poured or squeezed. The oral dosage form may also be a capsule or coated pellets, in which the drug is enclosed within either a hard or soft soluble container or "shell" made from a suitable form of gelatin. The drug, itself may be in the form of granules to which varying amount of coating have been applied or in a capsule coated extended release, in which the drug is enclosed within either a hard or soft soluble container or "shell" made from a suitable form of gelatin. Additionally, the capsule may be covered in a designated coating which releases a drug or drugs in such a manner to allow at least a reduction in dosing frequency as compared to that drug or drugs presented as a conventional dosage form.

The oral dosage form may further be a capsule delayed release, in which the drug is enclosed within either a hard or soft soluble container made from a suitable form of gelatin, and which releases a drug (or drugs) at a time other than promptly after administration, whereby enteric-coated articles are delayed release dosage forms. Capsule delayed release pellets, in which the drug is enclosed within either a hard or soft container or "shell" are also useful. In these cases, the drug itself is in the form of granules to which enteric coating has been applied, thus delaying release of the drug until its passing into the intestine. Capsule extended release and capsule film-coated extended release are also useful.

Additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule).

Typically, the active ingredients may be dissolved or suspended in a liquid vehicle, a granule (a small particle or grain), a pellet (a small sterile solid mass consisting of a highly purified drug, with or without excipients, made by the formation of granules, or by compression and molding), or a pellet coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form).

Other forms include pills (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant aftertaste), tablet coated or tablet delayed release, tablet dispersible, tablet effervescent, tablet extended release, tablet film coated, or tablet film coated extended release where the tablet is formulated in such manner as to make the contained medicament available over an extended period of time following ingestion.

In other forms, a tablet for solution, tablet for suspension, tablet multilayer, tablet multilayer extended release may be provided, where the tablet is formulated in such manner as to allow at least a reduction in dosing frequency as compared to that drug presented as a conventional dosage form. A tablet orally disintegrating, tablet orally disintegrating delayed release, tablet soluble, tablet sugar coated, osmotic, and the like are also suitable.

The oral dosage form composition may contain an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, the injectable and infusion dosage forms include, but are not limited to, a liposomal injectable, which either consists of or forms liposomes (a lipid bilayer vesicle usually composed of phospholipids which is used to encapsulate an active drug substance). An injection, which includes a sterile preparation intended for parenteral use; five distinct classes of injections exist as defined by the USP, is also suitable. An emulsion injection, which includes an emulsion consisting of a sterile, pyrogen-free preparation intended to be administered parenterally or a lipid complex injection are also suitable.

Other forms include a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution; a powder lyophilized for solution injection, which is a dosage form intended for the solution prepared by lyophilization ("freeze drying"), a process which involves the removal of water from products in the frozen state at extremely low pressures. This is intended for subsequent addition of liquid to create a solution that conforms in all respects to the requirements for injections; a powder lyophilized for suspension injection being a liquid preparation, intended for parenteral use that contains solids suspended in a suitable fluid medium and conforms in all respects to the requirements for Sterile Suspensions; the medicinal agents intended for the suspension are prepared by lyophilization ("freeze drying"), a process which involves the removal of water from products in the frozen state at extremely low pressures; a solution injection being a liquid preparation containing one or more drug, substances dissolved in a suitable solvent or mixture of mutually miscible solvents that is suitable for injection; a solution concentrate injection being, a sterile preparation for parenteral use which, upon the addition of suitable solvents, yields a solution conforming in all respects to the requirements for injections.

A suspension injection comprises a liquid preparation, suitable for injection, which consists of solid particles dispersed throughout a liquid phase in which the particles are not soluble that can also consist of an oil phase dispersed throughout an aqueous phase, or vice-versa. A suspension liposomal injection comprises a liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. A suspension sonicated injection comprises a liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles.

The parenteral carrier system includes one or more pharmaceutically suitable excipients, such as solvents and co-solvents, solubilizing agents, wetting agents, suspending agents, thickening, agents, emulsifying agents, chelating agents, buffers, adjusters, antioxidants, reducing agents, antimicrobial preservatives, bulking agents, protectants, tonicity adjusters, and special additives. Formulations suitable for parenteral administration conveniently comprise a sterile oily or aqueous preparation of the active ingredient which is preferably isotonic with the blood of the recipient.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols); foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged; metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and, aerosol spray being an aerosol product which utilizes a compressed gas as the propellant to provide the force necessary to expel the product as a wet spray and being applicable to solutions of medicinal agents in aqueous solvents.

As used herein, transdermal dosage forms include, but are not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and, other various types of transdermal patches such as matrix, reservoir and others known in the art.

As used herein, dosage forms include various dosage forms known in the art such as lotions (an emulsion, liquid dosage form, whereby this dosage form is generally for external application to the skin), lotion augmented (a lotion dosage form that enhances drug delivery, whereby augmentation does riot refer to the strength of the drug in the dosage form), gels (a semisolid dosage form that contains a gelling agent to provide stiffness to a solution or a colloidal dispersion, whereby the gel may contain suspended particles) and ointments (a semisolid dosage form, usually containing less than 20% water and volatiles and greater than 50% hydrocarbons, waxes, or polyols as the vehicle, whereby this dosage form is generally for external application to the skin or mucous membranes).

Ointment augmented (an ointment dosage form that enhances drug delivery, whereby augmentation does not refer to the strength of the drug in the dosage form), creams (an emulsion, semisolid dosage form, usually containing greater than 20% water and volatiles and/or less than 50% hydrocarbons, waxes, or polyols may also be used as the vehicle, whereby this dosage form is generally for external application to the skin or mucous membranes. Cream augmented (a cream dosage form that enhances drug delivery, whereby augmentation does not refer to the strength of the drug in the dosage form), emulsions (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release, pastes (a semisolid dosage form, containing a large proportion, 20-50%, of solids finely dispersed in a fatty vehicle, whereby this dosage form is generally for external application to the skin or mucous membranes), solutions (a clear, homogeneous liquid dosage form that contains one or more chemical substances dissolved in a solvent or mixture of mutually miscible solvents), and powders are also suitable.

Jellies (a class of gels, which are semisolid systems that consist of suspensions made up of either small inorganic particles or large organic molecules interpenetrated by a liquid—in which the structural coherent matrix contains a high portion of liquid, usually water) and films (a thin layer or coating), including film extended release (a drug delivery system in the form of a film that releases the drug, over an extended period in such a way as to maintain constant drug levels in the blood or target tissue) and film soluble (a thin layer or coating which is susceptible to being dissolved when in contact with a liquid) are also suitable.

Patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing, frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, linty acids, fatty acid esters and polyols), and the like. Various FDA-approved topical inactive ingredients are found at the FDA's "The Inactive Ingredients Database" that contains inactive ingredients specifically intended, as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

EXAMPLES

The following examples are presented for illustrative purposes only, and are not intended to limit the scope of the present invention in any way. The examples illustrate that 2MD, an analog of $1,25(OH)_2D_3$ originally suggested to be therapeutically useful in prevention and treatment of osteoporosis, is also therapeutically useful in treating primary hyperparathyroidism and/or in treating and/or preventing the symptoms of primary hyperparathyroidism in a patient in need thereof.

Reference is made to Zella et al., "Novel, Selective Vitamin D Analog Suppresses Parathyroid Hormone in Uremic Animals and Postmenopausal Women, Am J. Nephrology 2014; 39:476-483, May 17, 2014, the content of which is incorporated herein by reference in its entirety. Zella et al. discloses the results from a Phase 1B Dose-Finding Study in Postmenopausal Women in which the participants were administered various doses of 2MD and afterwards, serum parathyroid hormone (PTH) levels and serum calcium levels were monitored. In Zella et al.'s study, post-menopausal women were treated orally once daily with 2MD, calcitriol, or placebo for 28 days. Serum samples for PTH analysis were collected at baseline and 2, 7, 14, and 28 days after the first dose was administered.

Figure 1:
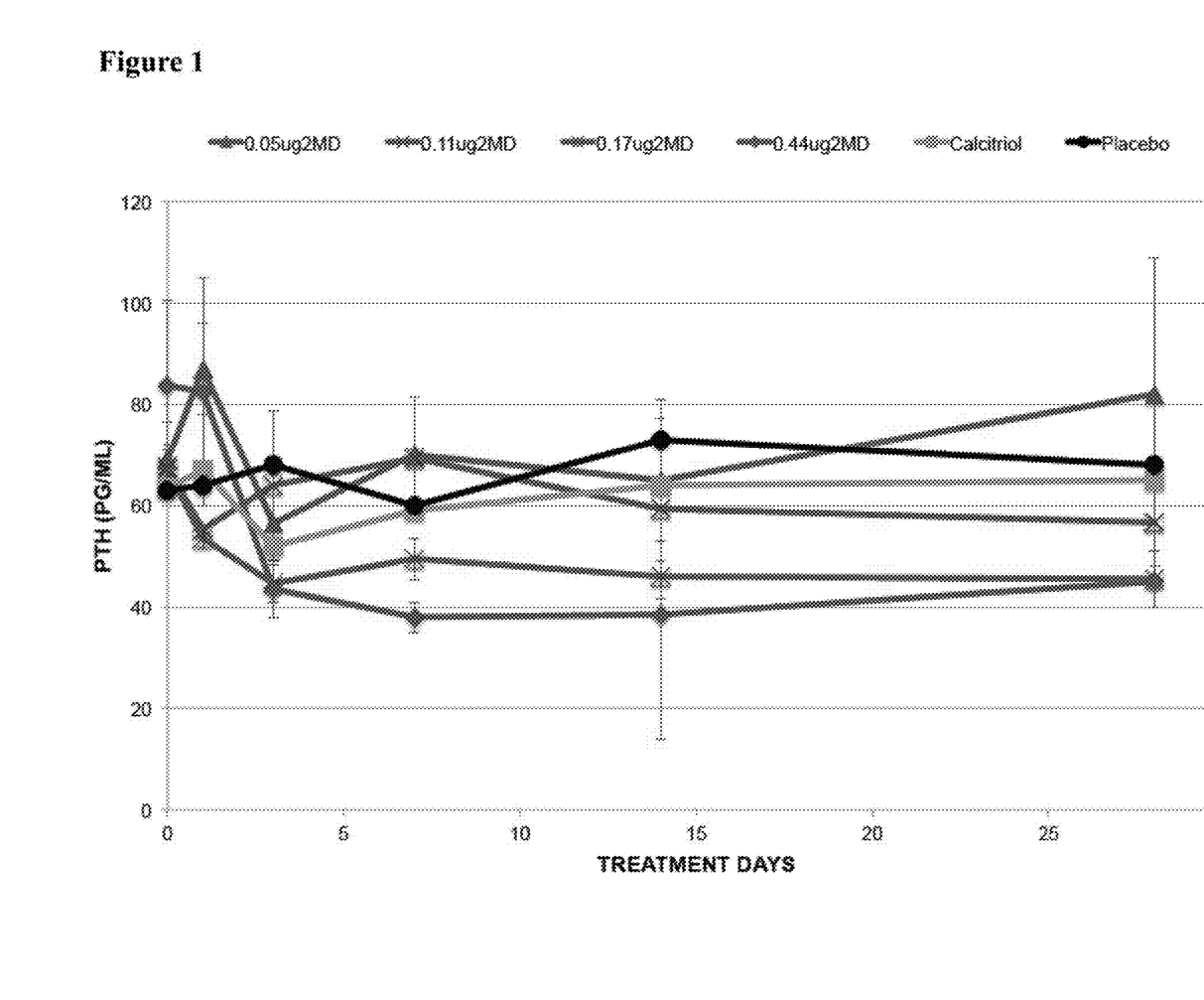
FIG. 1. Reduction in serum PTH levels versus days post-administering 2MD, calcitriol, or placebo to patients having or at risk for developing primary hyperparathyroidism.
Figure 2:
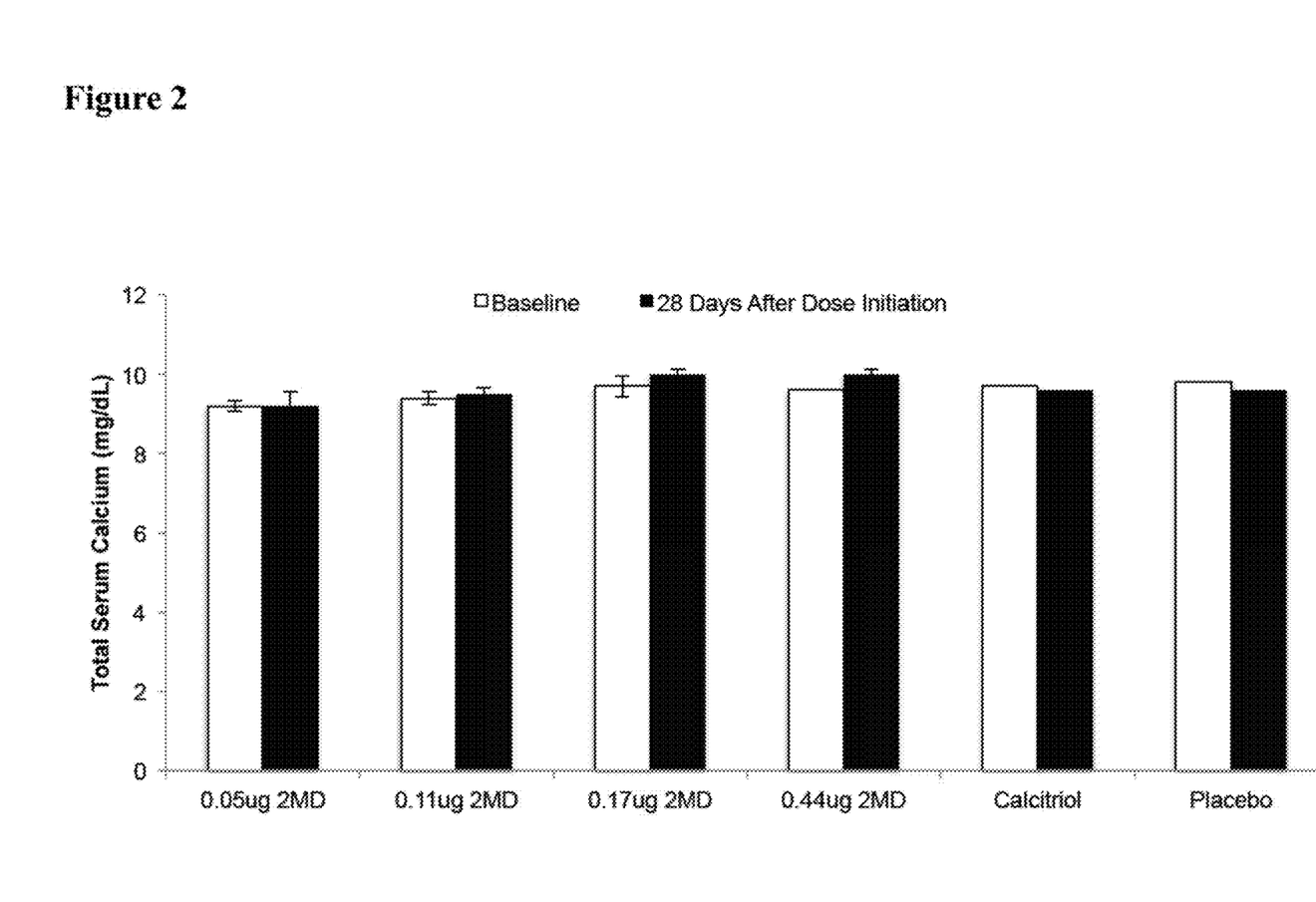
FIG. 2. Serum calcium levels at baseline and at 28 days post-administering 2MD, calcitriol, or placebo to patients having or at risk for developing primary hyperparathyroidism.
Figure 3:
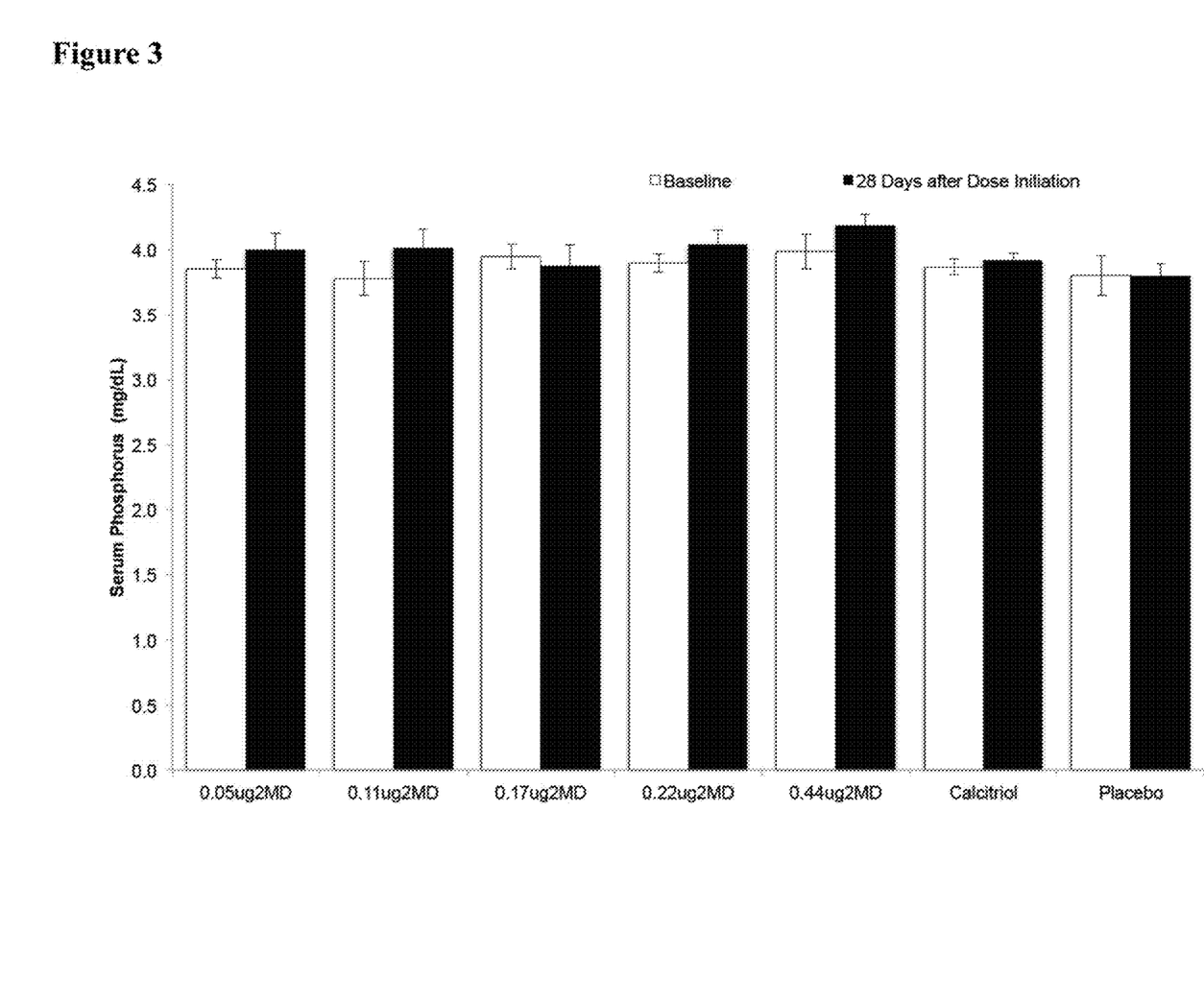
FIG. 3. Serum phosphate levels at baseline and at 28 days post administering 2MD, calcitriol, or placebo to patients having or at risk for developing primary hyperparathyroidism.

In FIG. 1 of the present application, the results from the Phase 1B Dose-Finding Study in Postmenopausal Women from Zella et al. were plotted using only data from subjects that would be classified as having primary hyperparathyroidism or on a watch list for having primary hyperparathyroidism (i.e., subjects having >60 pg/ml serum PTH at baseline). In FIG. 1, the number of subjects administered each dose of 2MD, calcitriol, or placebo, consisted of the following: 0.05 µg 2MD-2 subjects, 0.11 µg 2MD-3 subjects; 0.17 µg 2MD-4 subjects; 0.44 µg 2MD-2 subjects; 0.5 µg calcitriol-1 subject; and placebo-1 subject. As indicated, PTH levels in the subjects administered 2MD at: doses of 0.11 µg, 0.17 µg, and 0.4 µg decreased over time at a level corresponding, to the dose of 2MD. After 28 days, a dose of 2MD of 0.11 µg, 0.17 µg, and. 0.4 µg, resulted in a decrease in PTH of −7%, −31%, and −44%, respectively. After 28 days, a dose of 2MD of 0.05 µg, a dose of calcitriol of 0.5 µg, and the placebo resulted in no decrease in PTH, and actually resulted in a slight increase (i.e., a 16%, 15%, or 27% increase in PTH, respectively). None of the subjects in any group exhibited a rise in serum calcium levels or serum phosphate levels. (See FIG. 2 and FIG. 3). In summary, 2MD could be administered orally at a daily dose of 0.11 µg-0.44 µg to treat subjects having primary hyperparathyroidism or at risk, for developing primary hyperparathyroidism.

In the foregoing description, it will be readily apparent to one skilled in the art that varying substitutions and modifications ma be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Unless defined, otherwise all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue or prior invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of reducing serum parathyroid hormone levels in a subject having primary hyperparathyroidism and exhibiting elevated serum parathyroid hormone levels, the method comprising administering a therapeutically effective amount of 2-methylene-19-nor-(20S)-1α,25-dihydroxyvitamin $D_3$ or a pharmaceutically acceptable salt thereof to the subject wherein the serum parathyroid hormone levels in the subject are reduced without inducing hypercalcemia in the subject.

2. The method of claim 1, wherein the therapeutically effective amount ranges from about 0.5 ng/kg to about 20 ng/kg.

3. The method of claim 1, wherein the therapeutically effective amount ranges from about 1.0 ng/kg to about 10 ng/kg.

4. The method of claim 1, wherein the subject is administered the therapeutically effective amount daily.

5. The method of claim 1, wherein the subject is administered the therapeutically effective amount three times per week.

6. The method of claim 1, wherein prior to treatment the subject has a serum parathyroid hormone (PTH) level of greater than about 55 pg/ml.

7. The method of claim 1, wherein after treatment the subject has a serum parathyroid hormone (PTH) level that dose not exceed 55 pg/ml.

8. The method of claim 1, wherein the 2-methylene-19-nor-(20S)-1α,25-dihydroxyvitamin $D_3$ is formulated in an oral, topical, transdermal, parenteral, injection or infusion dosage form.

* * * * *

UNITED STATES PATENT AND TRADEMARK OFFICE
CERTIFICATE OF CORRECTION

| | |
|---|---|
| PATENT NO. | : 10,369,161 B2 |
| APPLICATION NO. | : 14/710744 |
| DATED | : August 6, 2019 |
| INVENTOR(S) | : Hector F. DeLuca et al. |

It is certified that error appears in the above-identified patent and that said Letters Patent is hereby corrected as shown below:

On the Title Page

Item (54) and in the Specification, Column 1, Line 2, Title, "1-ALPHA," should be --1-α,--.

Item (57), Abstract, "hyperparathyroidism in as subject" should be --hyperparathyroidism in a subject--.

In the Specification

Column 1, Line 45, "hypercalceinia" should be --hypercalcemia--.

Column 2, Line 64, "paraealcitol" should be --paracalcitol--.

Column 2, Line 66, "2114" should be --2014--.

Column 3, Line 54, "handsdermal" should be --transdermal--.

Column 4, Line 4, "dihydroxyvitamin (2MD)" should be --dihydroxyvitamin $D_3$ (2MD)--.

Column 7, Line 48, "as" should be --a--.

Column 11, Line 50, "buffers, adjusters," should be --buffers, pH adjusters,--.

Column 12, Line 24, "herein, dosage" should be --herein, topical dosage--.

Column 12, Line 29, "riot" should be --not--.

Column 13, Line 36, "linty" should be --fatty--.

Signed and Sealed this
Eighth Day of October, 2019

Andrei Iancu
*Director of the United States Patent and Trademark Office*

Column 14, Line 21, "Afler" should be --After--.

Column 14, Line 34, "ma be" should be --may be--.